United States Patent [19]

Kirkpatrick

[11] 4,273,574
[45] Jun. 16, 1981

[54] 2-[3-(4-CHLOROPHENOXY)PROPYLTHIO]-5-(1,3,3-TRIMETHYLUREIDO)-1,3,4-THIADIAZOLE AND USE AS A POST-EMERGENT HERBICIDE

[75] Inventor: Joel L. Kirkpatrick, Washington Crossing, Pa.

[73] Assignee: Gulf Oil Corporation, Pittsburgh, Pa.

[21] Appl. No.: 178,240

[22] Filed: Aug. 14, 1980

[51] Int. Cl.³ .................. A01N 43/82; C07D 285/12
[52] U.S. Cl. ........................................ 71/90; 548/140
[58] Field of Search ............................ 71/90; 548/140

[56] References Cited

U.S. PATENT DOCUMENTS

| 4,073,793 | 2/1978 | Arndt et al. | 71/90 |
| 4,086,077 | 4/1978 | Doyle, Jr. | 548/140 |
| 4,141,717 | 2/1979 | Kirkpatrick | 71/90 |
| 4,233,057 | 11/1980 | Lavanish | 71/90 |

Primary Examiner—Alton D. Rollins
Attorney, Agent, or Firm—Carl A. Cline

[57] ABSTRACT

A novel compound having the structural formula

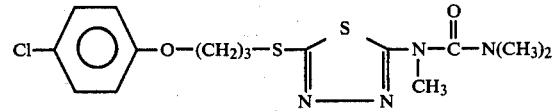

is disclosed, which is particularly useful as a post-emergent herbicide for combating unwanted vegetation in the presence of peanuts, rice and grain sorghum.

6 Claims, No Drawings

2-[3-(4-CHLOROPHENOXY)PROPYLTHIO]-5-(1,3,3-TRIMETHYLUREIDO)-1,3,4-THIADIAZOLE AND USE AS A POST-EMERGENT HERBICIDE

DESCRIPTION OF THE INVENTION

Highly active thiadiazoleurea herbicides of little or no selectivity are disclosed, for example, in U.S. Pat. No. 4,086,077. Other compounds with selectivity of a narrow, specific type which may be used in one or two crops are very desirable and have been disclosed, for example, in U.S. Pat. No. 4,141,717. Herbicides with specific selectivity are preferred because they give more efficient control of unwanted vegetation. However, there is a scarcity of herbicides of this type. For the most part, the selective herbicides in commercial use are useful in a larger number of crops but are not effective against a large number of weed species.

Briefly, I have discovered a novel compound having the structural formula

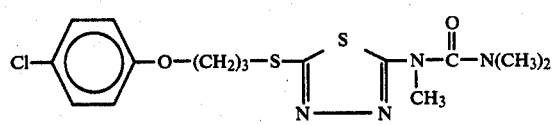

which is effective against many of the common pestiferous weed species and is particularly useful for post-emergent control of unwanted vegetation in peanuts, rice and grain sorghum.

The novel herbicide may be prepared from commercially available chemical intermediates by means of the reaction scheme outlined below.

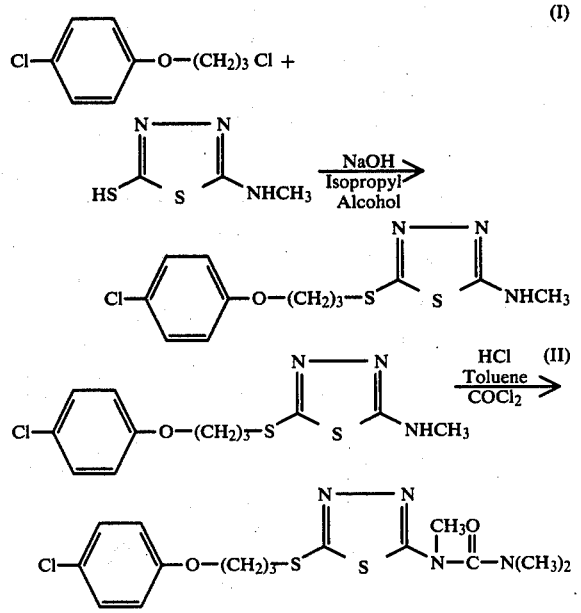

The method is illustrated by means of the following specific procedures.

To a mixture of 993.4 g. (6.75 moles) of 2-mercapto-5-methylamino-1,3,4-thiadiazole, 540 g. of 50% NaOH (6.75 mols), 3150 ml. of isopropyl alcohol and 1650 ml. of water is added 1258 g. (6.13 mols) of 3-(4'-chlorophenoxy) propyl chloride, and the resultant mixture is heated to reflux for 2 hours. Upon cooling to room temperature the contents of the reaction vessel are a solid mass. This is broken up, slurried with 3600 ml. of water, filtered and washed with water to give 1689 g. (91.3% yield) of the product, Compound (I) melting at 102.5°–104.5° C.

A solution of 452.8 g. (1.5 mols) of 2-(4'Chlorophenoxypropylthio)-5-methylamino-1,3,4-thiadiazole (m.p. 102°–5° C.) in 2250 ml. of toluene is treated with anhydrous HCl until the mixture becomes a very thick slurry. During this time the temperature of the mixture rises to about 40° C. An additional 500 ml. of toluene is added, the slurry is heated to 105° C. and, with stirring, a stream of phosgene is passed through the mixture. A total of 98.9 g. of phosgene is added over a 3 hour period, during which time the slurry thins and finally becomes a clear yellow solution. After cooling in an ice bath to 20° C. while sweeping nitrogen through the system, sufficient 40% aqueous dimethylamine (about 620 ml.) is added slowly, while keeping the temperature below 30° C., to bring the mixture to pH 9. The solution is washed successively with 350 ml. portions of water, 10% HCl and water again, then with two 500 ml. portions of 15% NaOH, dried over anhydrous sodium sulphate and the toluene is removed under vacuum, giving 551.5 g. of product (91.2% yield) as a heavy oil. (Compound II).

SELECTIVELY COMBATTING UNWANTED VEGETATION

The novel herbicide is particularly effective when used post-emergently against weeds in fields of peanuts, rice and grain sorghum. Greenhouse tests are described below to illustrate selective control of unwanted vegetation.

PROCEDURE

An aqueous dispersion of the herbicide compound was prepared by combining 0.4 gram of the compound with about 4 ml. of a solvent-emulsifier mixture (3 parts of a commercial polyoxyethylated vegetable oil emulsifier, one part xylene, one part kerosene) and then adding water, with stirring, to a final volume of 40 ml.

The species of plants on which the compound was tested were planted in disposable plastic pots in a greenhouse. Ten to eighteen days after emergence of the plants, three pots of each species were sprayed at each application rate with an aqueous dispersion of the active compound prepared as described above, at a rate of 1 lb. of active compound per acre and at a spray volume of 40 gal. per acre. Approximately one week after the spray application the plants were observed and phytotoxicity was rated according to the following schedule.

0—no control or injury
1—1 to 25 percent control or injury
2—26 to 75 percent control or injury
3—76 to 99 percent control or injury
4—complete control or kill Results of tests of the herbicide on 24 species are tabulated below.

TABLE 1

Results of Use of 2-[3-(4-Chlorophenoxy)propylthio]-5-(1,3,3-trimethylureido)-1,3,4-thiadiazole Post-Emergently at 1 lb. per Acre

| Plant Species | Rating |
| --- | --- |
| Cocklebur (*Xanthium pensylvanicum*) | 4 |
| Lambsquarters (*Chenopodium album*) | 4 |
| Morning Glory (*Ipomea purpurea*) | 4 |
| Pigweed (*Amaranthus retroflexus*) | 4 |

TABLE 1-continued

Results of Use of 2-[3-(4-Chlorophenoxy)propylthio]-5-(1,3,3-trimethylureido)-1,3,4-thiadiazole Post-Emergently at 1 lb. per Acre

| Plant Species | Rating |
|---|---|
| Wild Buckwheat (Polygonum convolvulus) | 4 |
| Wild Mustard (Brassica kaber) | 4 |
| Barnyard Grass (Echinochloa crusgalli) | 2 |
| Crabgrass (Digitaria sanguinalis) | 2 |
| Downy Brome (Bromus tectorum) | 3 |
| Giant Foxtail (Setaria faberii) | 3 |
| Green Foxtail (Setaria viridis) | 4 |
| Nutsedge (Cyperus esculentus) | 1 |
| Shattercane (Sorghum bicolor) | 2 |
| Wild Oats (Avena fatua) | 4 |
| Alfalfa (Medicago sativa) | 4 |
| Cotton (Gossypium herbaceum) | 4 |
| Peanut (Arachis hypogaea) | 2 |
| Soybean (Soja max) | 4 |
| Sugar Beet (Beta vulgaris) | 4 |
| Tomato (Lycopersicum esculentum) | 4 |
| Corn (Zea mays) | 3 |
| Grain Sorghum (Sorghum vulgare) | 2 |
| Rice (Oryza sativa) | 2 |
| Wheat (Triticum aestivum) | 4 |

The herbicidal compound is effective at lower application rates than 1 lb. per acre. The herbicide was applied to 12 species at lower rates, according to the procedure described above. The herbicidal injury was scored on a schedule of zero (no injury) to 10 (complete kill). The results are tabulated below.

TABLE 2

RESULTS OF POST-EMERGENT USE OF THE HERBICIDE AT LOW APPLICATION RATES

| Plant Species | Score at ¼ lb/A. | Score at ⅛ lb/A. | Score at 1/16 lb/A. |
|---|---|---|---|
| Pigweed (Amaranthus retroflexus) | 10 | 10 | 10 |
| Alfalfa (Medicago sativa) | 10 | 6 | 4 |
| Tomato (Lycopersicum esculentum) | 10 | 10 | 6 |
| Cotton (Gossypium herbaceum) | 10 | 10 | 10 |
| Soybean (Soja max) | 10 | 10 | 10 |
| Peanut (Arachis hypogaea) | 2 | 2 | 1 |
| Yellow Foxtail (Setaria glauca) | 2 | 0 | 0 |
| Smartweed (Polygonum pensylvanicum) | 10 | 10 | 10 |
| Velvet Leaf (Abutilon cheophrasti) | 10 | 10 | 10 |
| Jimson Weed (Datura stramonium) | 10 | 10 | 10 |
| Morning Glory (Ipomea purpurea) | 10 | 10 | 9 |
| Cocklebur (Xanthium pensylvanicum) | 10 | 10 | 10 |

The test results disclosed above serve to illustrate the selectivity and efficacy of the novel herbicide. These data will enable a worker in the art to make a selection of application rates and form a judgment as to whether the herbicide is suitable for a particular crop and weed problem. It may be seen, for example, that application rates as low as 1 oz. per acre are sufficient to control certain specific weeds, whereas as much as 1 lb. per acre may be necessary to combat other species. It may be preferable to use the herbicide at a low rate in combination with another efficient herbicide of different selectivity in some situations. It will be understood that higher rates of application may be required to combat vegetation which has become toughened by growth under adverse climatic conditions.

In general, formulations of the herbicide desirably contain from 0.1 percent to 95 percent by weight of the active compound of formula (II) and from 0.1 to 75 percent by weight of a carrier or surfactant, the more dilute formulations being usually in the form of sprays, ready for application to plants. The more concentrated formulations are most conveniently prepared as emulsifiable concentrates or wettable powders which may be diluted with a relatively large amount of water to make spray mixtures.

Wettable powders comprise intimate, finely divided mixtures of the herbicide, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the herbicide comprise in each instance, a solution of herbicide compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

I claim:

1. 2-[3-(4-Chlorophenoxy)propylthio]-5-(1,3,3-trimethylureido)-1,3,4-thiadiazole.

2. A herbicidal formulation which comprises from 0.1 percent to 95 percent by weight of the compound of claim 1 in combination with from 0.1 to 75 percent by weight of a carrier or surface active agent.

3. The method of selectively combating unwanted vegetation which comprises applying to said vegetation an effective amount of the compound of claim 1.

4. The method of claim 3 in which unwanted vegetation is combated in the presence of a growing crop of peanuts.

5. The method of claim 3 in which unwanted vegetation is combated in the presence of a growing crop of rice.

6. The method of claim 3 in which unwanted vegetation is combated in the presence of a growing crop of grain sorghum.

* * * * *